US012622740B2

(12) United States Patent
Germain

(10) Patent No.: US 12,622,740 B2
(45) Date of Patent: May 12, 2026

(54) ELECTROSURGICAL DEVICE WITH KNIFE EDGE

(71) Applicant: Relign Corporation, Santa Clara, CA (US)

(72) Inventor: Aaron Germain, San Jose, CA (US)

(73) Assignee: Relign Corporation, Santa Clara, CA (US)

( * ) Notice: Subject to any disclaimer, the term of this patent is extended or adjusted under 35 U.S.C. 154(b) by 398 days.

(21) Appl. No.: 18/201,483

(22) Filed: May 24, 2023

(65) Prior Publication Data

US 2023/0380884 A1 Nov. 30, 2023

Related U.S. Application Data

(60) Provisional application No. 63/346,417, filed on May 27, 2022.

(51) Int. Cl.
*A61B 18/14* (2006.01)
*A61B 18/00* (2006.01)

(52) U.S. Cl.
CPC .... *A61B 18/14* (2013.01); *A61B 2018/00601* (2013.01); *A61B 2018/1467* (2013.01); *A61B 2218/007* (2013.01)

(58) Field of Classification Search
CPC ................. A61B 18/14; A61B 18/148; A61B 2017/00477; A61B 2018/00178; A61B 2018/00196; A61B 2018/00601; A61B 2018/00607; A61B 2018/1467; A61B 2218/007

USPC .......................................................... 606/45
See application file for complete search history.

(56) References Cited

U.S. PATENT DOCUMENTS

| | | | | |
|---|---|---|---|---|
| 5,441,498 A * | 8/1995 | Perkins | ............. | A61B 18/1442 |
| | | | | 604/35 |
| 6,648,839 B2 * | 11/2003 | Manna | ............... | A61B 18/1402 |
| | | | | 601/3 |
| 6,958,062 B1 * | 10/2005 | Gough | ................ | A61B 18/148 |
| | | | | 606/41 |
| 7,553,309 B2 * | 6/2009 | Buysse | ............. | A61B 18/1206 |
| | | | | 606/41 |
| 8,052,679 B2 * | 11/2011 | Young | .................. | A61B 18/148 |
| | | | | 606/41 |
| 2006/0100614 A1 * | 5/2006 | Long | .................. | A61B 18/1477 |
| | | | | 606/41 |
| 2017/0056099 A1 * | 3/2017 | Hubelbank | ........ | A61B 18/1477 |
| 2018/0263649 A1 | 9/2018 | Germain et al. | | |
| 2018/0303509 A1 | 10/2018 | Germain et al. | | |
| 2018/0317957 A1 | 11/2018 | Germain et al. | | |
| 2019/0008538 A1 | 1/2019 | Germain et al. | | |
| 2019/0008541 A1 | 1/2019 | Norton et al. | | |
| 2019/0015151 A1 | 1/2019 | Germain et al. | | |
| 2019/0021788 A1 | 1/2019 | Germain et al. | | |
| 2019/0059983 A1 | 2/2019 | Germain et al. | | |
| 2019/0083121 A1 | 3/2019 | Benamou et al. | | |

(Continued)

*Primary Examiner* — Michael F Peffley
(74) *Attorney, Agent, or Firm* — Schwegman Lundberg & Woessner, P.A.

(57) ABSTRACT

An electrosurgical device for treating tissue have a sharp forming a distal end thereof. The electrosurgical device can include two or more electrodes spaced from the sharp that can each reciprocate. Other arrangements for the two or more electrodes such as those that do not reciprocate but are held stator relative to the sharp are contemplated.

19 Claims, 8 Drawing Sheets

(56)          References Cited

U.S. PATENT DOCUMENTS

2019/0134279 A1      5/2019  Benamou et al.
2025/0195122 A1*    6/2025  Germain ............. A61B 18/148

* cited by examiner

110

120

125

112

128

ELECTROSURGICAL DEVICE WITH KNIFE EDGE

CLAIM OF PRIORITY

This application claims the benefit of U.S. Provisional Patent Application Ser. No. 63/346,417, filed on May 27, 2022, the benefit of priority of which is claimed hereby, and which is incorporated by reference herein in its entirety.

FIELD OF THE INVENTION

The present invention relates generally to apparatuses for surgical procedures and, more particularly, to apparatuses to surgically cut tissue such as bone and soft tissue.

BACKGROUND

A variety of surgical apparatuses exist for endoscopic cutting and removal of bone including for subacromial decompression, anterior cruciate ligament reconstruction involving notchplasty, and arthroscopic resection of the acromioclavicular joint. Currently, surgeons use arthroscopic shavers and burrs having rotational cutting surfaces to remove hard tissue in such procedures.

A need exists for endoscopic cutting instruments that remove tissue rapidly.

Overview

The present invention provides improved tissue cutting devices, systems and methods for their use, where the likelihood of electrical arching during resection of tissue is greatly reduced. The devices, systems and methods may utilize one or more of a number of separate features, described in details below. Many endoscope probes in use include lumens within rotatable shafts for the vacuum aspiration of fluid including tissue debris from the working site. Many of these tools also rely on the delivery of monopolar radiofrequency (RF) current from the handpiece to the working end of the probe for coagulation or ablation. With such monopolar arrangement, current must be passed from the working end of the probe through tissue to an electrical grounding pad worn by the patient.

The present inventor has developed improved surgical apparatuses and systems, with a thin distal edge cutting profile (such as that of a scalpel, forceps, trocar, etc.). This configuration provides that the apparatuses and systems are tissue sparing and that they have better manipulation capability for controlled cutting of tissue. Typically, a thin distal edge cutting profile with an electrosurgical device would result in an incomplete circuit with electrical arcing, as at least one of a pair of electrodes would not be in contact with tissue. However, the present inventor has recognized that the pair of electrodes operate as a bipolar electrode pair if closely arranged together and if the pair of electrodes are reciprocated in a rapid manner (e.g., between 2,500 to 30,000 RPM, inclusive). More particularly, the present inventor has invented an arrangement where a first of the pair of electrodes can be positioned on a first side of a distal edge or distal point (also referred to as a distal tip or sharp herein) and a second of the pair of electrodes can be positioned on a second side of the distal edge or distal point. The pair of electrodes can reciprocate such that the first of the pair of electrodes can be extended distally beyond the distal edge or distal point while the second of the pair of electrodes can be retracted proximally of the distal edge or distal point, and vice versa. Thus, one of the first or second of the pair of electrodes can extend distally of the distal edge or distal point while the other of the first of the pair of first or second of the pair electrodes can be proximal of the distal edge or distal point. Reciprocal movement of the pair of electrodes can be extremely rapid such that surgical apparatus shifts from passing current to the tissue to electrically isolated and back to passing current such that arcing between the pair of electrodes is impossible.

The present inventor has developed improved surgical apparatuses and systems, such as with the combined capability to perform coagulation, endoscopic tissue cutting using RF and fluid removal. The present inventor further has developed a system wherein a reusable handpiece may be removably connected to the replaceable, usually disposable, probe while permitting the various functions discussed above while allowing for vacuum aspiration of fluids including tissue debris and smoke through a probe shaft and outwardly through the handpiece without interfering with the electrical and/or mechanical operation of the surgical system to deliver radiofrequency (RF) current to the probe. The present inventor contemplates the surgical apparatuses and systems can have the pair of electrodes be bipolar to allow for the use of RF in sensitive environments such as in neurological, spinal and cardiac applications where the use of RF was not thought possible among other benefits.

Relevant commonly owned patent publications include: US 2018-0303509; US 2019-0008541; US 2019-0059983; US 2019-0134279; US 2019-0021788; US 2018-0317957; US 2019-0008538; US 2019-0083121; US 2018-0263649; and US 2019-0015151, the full disclosures of which are incorporated herein by reference.

The following, non-limiting examples (referred to as aspects/techniques), detail certain aspects of the present subject matter to solve the challenges and provide the benefits discussed herein, among others.

In some aspects, the techniques described herein relate to a probe for an electrosurgical device for treating tissue, the probe including: a tip having a sharp at a distal most end thereof; a first electrode adjacent the sharp on a first side thereof; and a second electrode adjacent the sharp on a second side thereof, wherein the first electrode is spaced from the second electrode; wherein the first electrode and the second electrode are configured to reciprocate relative to the tip to selectively move between a first configuration where a distal end of first electrode is distal of the sharp and a distal end of the second electrode is proximal of the sharp and a second configuration where the distal end of the first electrode is proximal of the sharp and the distal end of the second electrode is distal of the sharp.

In some aspects, the techniques described herein relate to a probe, wherein the sharp includes an edge and the tip includes a first distal face extending laterally and longitudinally from the edge and a second distal face extending laterally and longitudinally from the edge, wherein the first distal face includes a first aperture receiving the first electrode and the second distal face includes a second aperture receiving the second electrode.

In some aspects, the techniques described herein relate to a probe, wherein at least one of the first distal face or the second distal face includes at least a port configured for vacuum aspiration of fluid including tissue debris from adjacent the tip.

In some aspects, the techniques described herein relate to a probe, further including an elongate outer shaft having a proximal end, a distal end and defining one or more passages extending therein from the proximal end to the distal end, wherein the tip is coupled to or forms the distal end of the outer shaft.

In some aspects, the techniques described herein relate to a probe, wherein at least one of the one or more passages is in fluid communication with the port.

In some aspects, the techniques described herein relate to a probe, wherein the first electrode is spaced from the second electrode by between 0.02 inches and 0.08 inches, inclusive.

In some aspects, the techniques described herein relate to a probe, wherein the tip is an electrically non-conductive material.

In some aspects, the techniques described herein relate to a probe, wherein the tip is a ceramic or ceramic composite.

In some aspects, the techniques described herein relate to a probe, wherein the first electrode and the second electrode are tungsten or an alloy containing tungsten.

In some aspects, the techniques described herein relate to a probe, wherein the first electrode and the second electrode have a diameter of between 0.01 inches and 0.02 inches, inclusive.

In some aspects, the techniques described herein relate to a probe, wherein the distal end of the first electrode and the second electrode is moved distal of the sharp by between inches and 0.25 inches, inclusive.

In some aspects, the techniques described herein relate to a probe, further including an illumination device adjacent the tip.

In some aspects, the techniques described herein relate to a probe, further including a cam mechanism and a linkage arm, wherein the cam mechanism is coupled to one of the first electrode and the second electrode and the linkage arm is coupled to both the first electrode and the second electrode.

In some aspects, the techniques described herein relate to a probe, wherein the cam mechanism includes a surface with undulations.

In some aspects, the techniques described herein relate to a probe, further including a handle, wherein the probe is configured to couple with the handle.

In some aspects, the techniques described herein relate to a probe, wherein the probe is configured with an electrosurgical coagulation mode that halts reciprocation of the first electrode and the second electrode and positions the first electrode and the second electrode in a substantially stationary arrangement adjacent the sharp.

In some aspects, the techniques described herein relate to a probe, wherein in the electrosurgical coagulation mode a distal end of the first electrode and a distal end of the second electrode are substantially flush with a tip of the sharp.

In some aspects, the techniques described herein relate to a probe, wherein the reciprocation of the first electrode and the second electrode is between 1,000 RPM to 30,000 RPM, inclusive.

In some aspects, the techniques described herein relate to a probe, the first electrode serves as a first polarity electrode and the second electrode serves as a second polarity electrode of a bipolar electrode pair.

In some aspects, the techniques described herein relate to a probe, wherein at least one of the first electrode and the second electrode is in selective contact with the tissue at any point during the treating of the tissue.

In some aspects, the techniques described herein relate to a probe, wherein the probe is configured for electrosurgical resection and electrosurgical coagulation of the tissue.

In some aspects, the techniques described herein relate to a probe, wherein the sharp is one of an edge or a point.

The foregoing aspects including the probe or elements of the probe can be combined in any combination.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to electrosurgical devices. Several embodiments of the electrosurgical devices will now be described to provide an overall understanding of the principles of the form, function and methods of use. In general, the present disclosure provides for electrosurgical devices that can be used as arthroscopic tools. In some cases, the electrosurgical devices described herein can perform more than one surgical function. Thus, the electrosurgical devices can be configured for coagulation and/or cutting bone such as of soft tissue, meniscal tissue, bone, etc. using RF energy. The arthroscopic tools are typically disposable and are configured for detachable coupling to a non-disposable handpiece. This description of the general principles of this invention is not meant to limit the inventive concepts in the appended claims.

Figure 1:
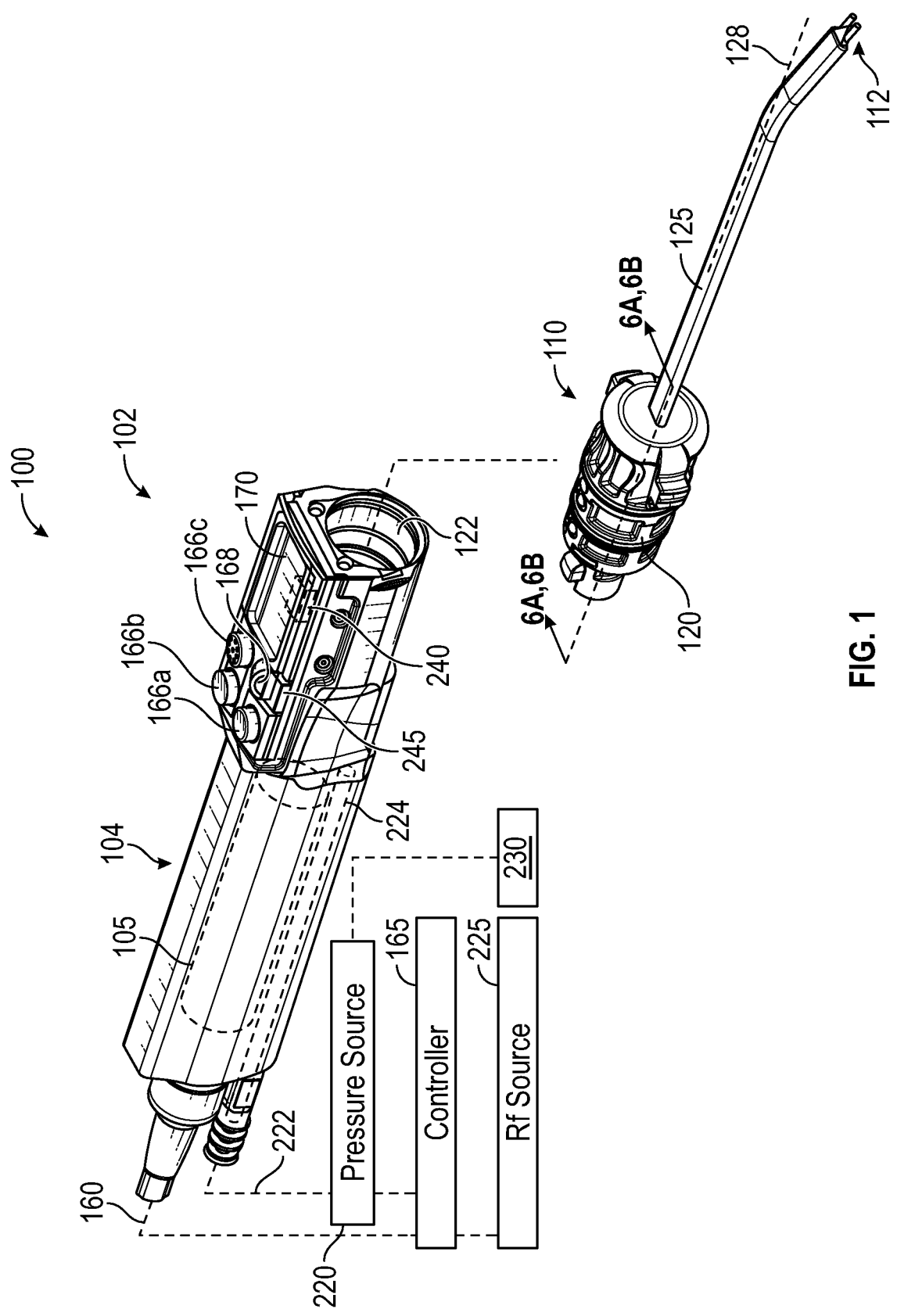
FIG. 1 is an exploded view of an arthroscopic cutting system that includes an electrosurgical device having reusable handpiece with a detachable single-use probe according to an example of the present disclosure.

In one example shown in FIG. 1, an arthroscopic system 100 of the present invention provides an electrosurgical apparatus 102 having a handpiece 104 with motor drive 105 and a probe 110 with a proximal hub 120 that can be received by receiver or bore 122 in the handpiece 104. In one aspect, the probe 110 has a working or distal end 112 that carries RF electrodes configured for use in many arthroscopic surgical applications, including but not limited to treating bone in shoulders, knees, hips, wrists, ankles and the spine.

Figure 2:
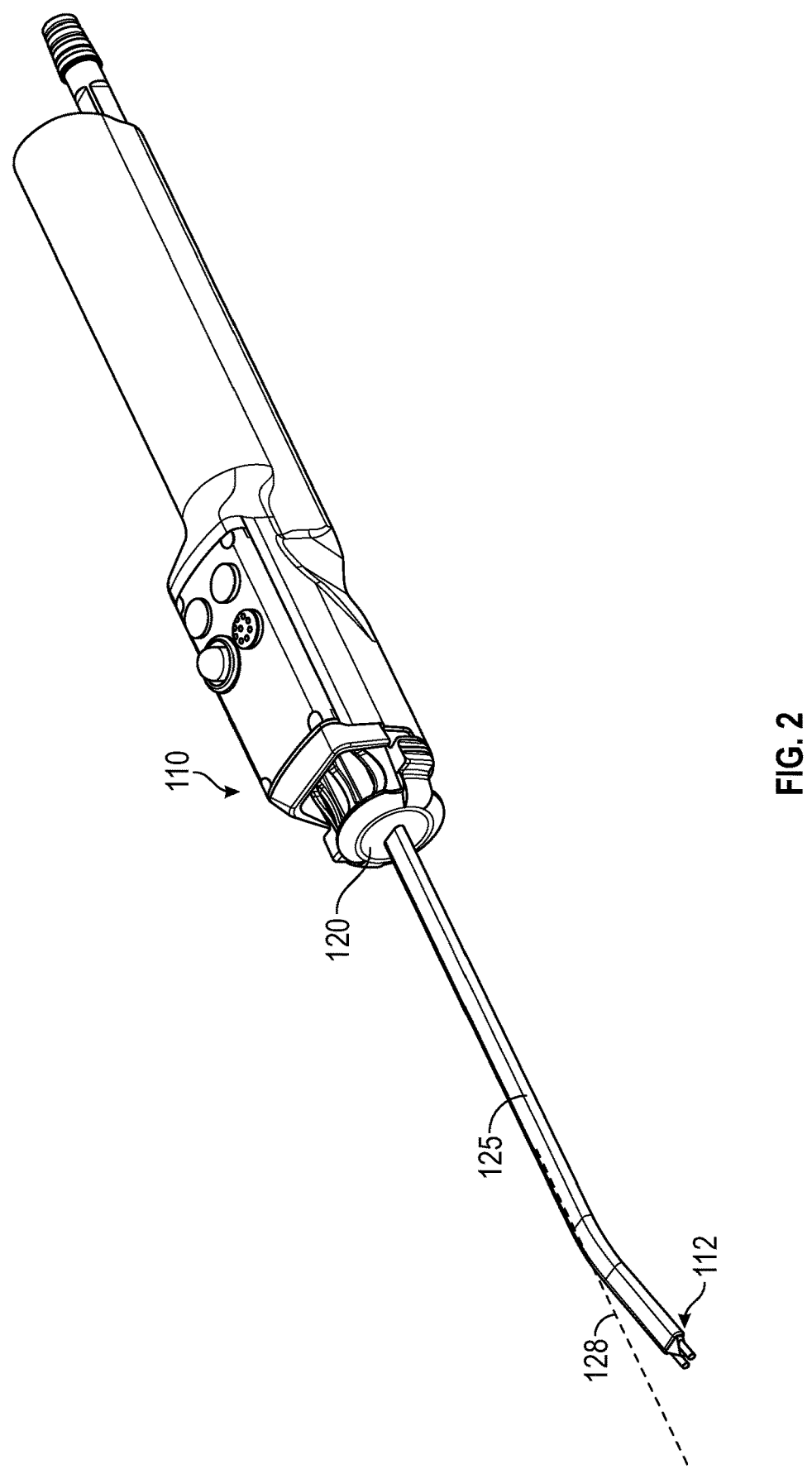
FIG. 2 is a perspective view of the electrosurgical device of FIG. 1 with the handpiece coupled to the probe according to an example of the present disclosure.

As can be seen in FIGS. 1 and 2, the probe 110 is attachable to and detachable from the handpiece 104. In FIGS. 1 and 2, the probe 110 has a sleeve or outer shaft 125 extending along longitudinal axis 128. A distal portion of the shaft 125 including the distal end 112 can be angled (e.g., by 15 degrees, or the like) relative to the longitudinal axis 128. However, angulation of the distal end 112 is not required. The shaft 125 can be somewhat flexible or rigid as desired and can house various components that can extend from the hub 120 to the distal end 112 as further discussed. Thus, the shaft 125 can comprise tube or outer sleeve with components such as wires, flow channels, additional shafts, and the like passing therethrough. The shaft 125 extends from the hub 120 (located at a proximal end of the shaft 125) to the distal end 112. The shaft 125 can be coupled in a fixed manner to the hub 120 which can be an injection molded plastic, for example, with the shaft 125 insert molded therein. One or more components can pass through the shaft 125 including to provide RF energy to the electrodes, provide for fluid removal, provide for fluid application, provide for illumination or the like.

In FIG. 1, it can be seen that the handle 104 is operatively coupled by electrical cable 160 to a controller 165 which can control the motor drive unit 105, communication with a pressure source 220, and communication with the RF source 225. Actuator buttons 166a, 166b, 166c, etc. on the handpiece 104 (sometimes called a handle herein) can be used to select operating modes, such as current strength for RF, motor speed, flow control, illumination control or the like. In one variation, a joystick 168 can be moved forward and backward to adjust the rotational speed of motor or other function. Motor speed can continuously adjustable, or can be adjusted in increments or can be halted for operation is some modes such as a coagulation mode. An LCD screen 170 can provided in the handpiece 104 for displaying operating parameters, such as mode of operation, etc.

It can be understood from FIG. 1 that the system 100 and handpiece 104 can be configured for use with various disposable probes which can be designed for various differ ent functions and procedures. Some of the probes can utilize the motor drive 105, for example, and some may not. These probes are various described in the various applications incorporated by reference with the U.S. Application Publications noted above.

FIG. 1 further shows that the system 100 also includes a pressure source 220 such as a negative pressure source coupled to aspiration tubing 222 which communicates with a flow channel 224 in handpiece 104 and can cooperate with one or more lumens of the probe 110. The system 100 includes the RF source 225 which can be connected to an electrode arrangement of the probe 110. The controller 165 and microprocessor therein together with control algorithms are provided to operate and control all functionality, which includes controlling the motor drive 105, the RF source 225, the flow inducing device 226, illuminating device, and the negative pressure source 220 which can aspirate fluid including tissue debris to collection reservoir 230.

As can be understood from the above description of the system 100, the electrosurgical device 102 and handpiece 104, the controller 165 and controller algorithms can be configured to perform and automate many tasks to provide for system functionality. In a first aspect, controller algorithms are needed for device identification so that when any of the different probes types are coupled to handpiece 104, the controller 165 will recognize the probe type and then select algorithms for operating the motor drive 105, RF source 225, negative pressure source 220, etc. as is needed for the particular probe. In a second aspect, the controller 165 can be configured with algorithms that identify whether the probe is coupled to the handpiece 104 in a particular orientation relative to the handpiece, wherein each orientation requires a different subset of the operating algorithms.

Referring to FIG. 1, the handpiece 104 can carry a first Hall effect sensor 240 in a distal region of the handpiece 104 adjacent the bore 122 that receives the hub 120 of probe 110. The handpiece 104 can carry a second Hall effect sensor 245 adjacent the rotatable drive coupling 150 of the probe 110. The probe 110 can carry a plurality of magnets that interact with the Hall effect sensors 240, 245 to provide multiple control functions in cooperation with controller algorithms, including (i) identification of the type of probe coupled to the handpiece, and (ii) the orientation of the probe hub 120 relative to the handpiece 104.

The Hall sensor 240 and controller algorithms can be adapted to read the magnetic field strength of the particular magnet(s) in the probe which can be compared to a library of field strengths that correspond to particular probe types. Then, a Hall identification signal can be generated or otherwise provided to the controller 165 to select the controller algorithms for operating the identified probe, which can include parameters for operating the motor drive 105, negative pressure source 220, the flow inducing device 226, power source (e.g., for illumination and other function) and/or RF source 225 as may be required for the probe type. The Hall sensor 240 and associated algorithms look for magnetic field strength regardless of polarity to identify the probe type.

As an example, the electrosurgical device 102 can be operated in different RF modes. As described below, a one mode can deliver RF current in a cutting waveform to thereby create a plasma that ablates tissue. Such mode can be utilized with the configurations of FIGS. 3A-6B, 8A and 8B, for example. The delivery of the RF current can be in a monopolar or bipolar manner. Thus, according to some examples discussed herein a first electrode serves as a first polarity electrode and a second electrode serves as a second polarity electrode of a bipolar electrode pair. In another RF mode, the controller 165 can include an algorithm that utilizes both electrodes in fixed/stationary position such as shown in FIGS. 7 and 7A. Then RF current in a coagulation waveform can be delivered to the first and second electrodes. The operator can then move the stationary electrodes over a targeted site for coagulation of tissue.

Figure 3A:
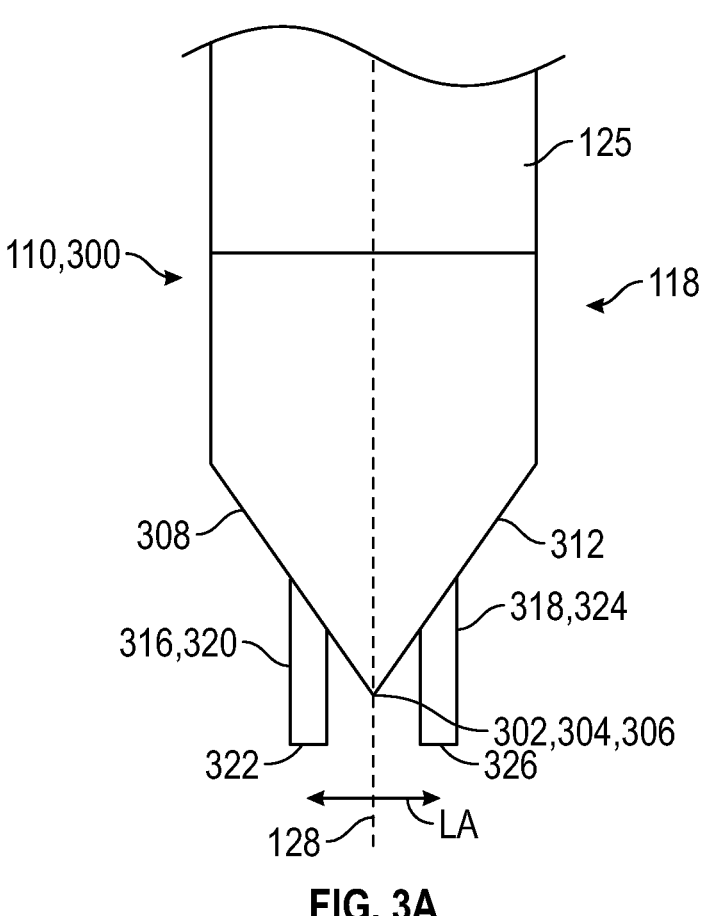
FIG. 3A is an enlarged first plan view of a distal (working) end of the probe of FIG. 2 showing various components thereof according to an example of the present disclosure.
Figure 3B:
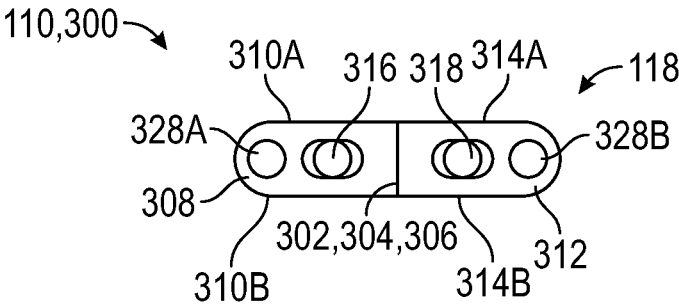
FIG. 3B is an enlarged second plan view of a distal (working) end of the probe of FIG. 3A showing various components thereof according to an example of the present disclosure.

FIGS. 3A and 3B show an example of the distal end 112 of the shaft 125 of the probe 110. A tip component 300 can be part of the shaft 125 or can be a separate component coupled to the distal end 112. The tip component 300 can be made of or coated with an electrically insulating material such as ceramic, for example. The tip component 300 can be configured with a sharp 302 such as at a distal end 304 thereof. The sharp 302 can be configured for mechanically treating tissue such as by cutting or puncturing, for example. Thus, the sharp 302 can be an edge, point, plurality of edges or have another configuration as known in the art. FIGS. 3A and 3B shows the sharp 302 provided with a cutting edge 306 (a knife edge) at the distal end 304.

As shown in FIG. 3A, the tip component 300 can have a first face 308 extending laterally (LA) and longitudinally with respect to the longitudinal axis 128 from the sharp 302 (here the cutting edge 306). Thus, the first face 308 can extend proximally and laterally LA away from the cutting edge 306. The first face 308 can be configured to have a desired angle relative to the longitudinal axis 128. The tip component 300 can have one or more edges 310A, 310B (FIG. 3B). These one or more edges 310A, 310B can surround or comprise edge(s) for the first face 308, for example. The one or more edges 310A, 310B can be configured as cutting edges, for example.

The tip component 300 can have a second face 312 extending laterally LA and longitudinally with respect to the longitudinal axis 128 from the sharp 302. The second face 312 can be on an opposing lateral side of the sharp 302 (here the cutting edge 306) from the first face 308. The second face 312 can extend proximally and laterally LA away from the edge 306. The second face 312 can be configured to have a desired angle relative to the longitudinal axis 128. The tip component 300 can have one or more edges 314A, 314B (FIG. 3B). These one or more edges 314A, 314B can surround or comprise edge(s) for the second face 312, for example. The one or more edges 314A, 314B can be configured as cutting edges, for example.

A first electrode 316 and a second electrode 318 can selectively protrude from the tip component 300. More particularly, the first electrode 316 can protrude from the first face 308 and the second electrode 318 can protrude from the second face 312. The first electrode 316 can be positioned adjacent the sharp 302 (the edge 306) and the second electrode 318 can be positioned adjacent the sharp 302 (the edge 306). The first electrode 316 and the second electrode 318 can be substantially equidistant from the sharp 302 (the edge 306). The first electrode 316 can be between 0.005 and 0.25 inches (0.127 mm and 6.35 mm) from the sharp 302. The second electrode 318 can be similarly arranged between 0.005 and 0.1 inches (0.127 mm and 2.54 mm) from the sharp 302. The first electrode 316 can be spaced between 0.01 and 0.2 inches (0.254 mm and 5.08 mm) from the second electrode 318.

The first electrode 316 and the second electrode 318 can have an elongate length along the longitudinal axis 128 and can extend generally parallel with one another with respect to the longitudinal axis 128. The first electrode 316 and the second electrode 318 can selectively protrude a distance from the first face 308 and the second face 312, respectively.

However, the first electrode 316 and the second electrode 318 can be selectively moveable relative to the respective first face 308 and second face 312 (and the sharp 302 at the distal end 304) according to one operation mode as further discussed herein.

As shown in FIG. 3A, the first electrode 316 can have a body 320 with a cylindrical shape and a distal end 322 with a domed (semi-spherical), point, inverted dome, jagged or flat tip. Other shapes for the body 320 and the distal end 322 are contemplated. Similarly, the second electrode 318 can have a body 324 with a cylindrical shape and a distal end 326 with a domed (semi-spherical), point, inverted dome, jagged or flat tip. Other shapes for the body 324 and the distal end 326 are contemplated. The first electrode 316 and the second electrode 318 can have a diameter of between 0.01 inches and 0.03 inches (0.254 mm and 0.762), inclusive. The first electrode 316 and the second electrode 318 can be constructed of electrically conductive metal or metal alloy such as tungsten, alloys including tungsten, or the like. The first electrode 316 and the second electrode 318 can be configured for bipolar operation with the first and second electrode 316, 318 alternating between active and return. Level of RF energy to the first and second electrodes 316, 318 can be controlled as desired for use in coagulation or RF ablation as known in the art.

The first electrode 316 can have substantially a same shape as the second electrode 318 (and hence substantially a same surface area). However, it is contemplated that in some examples the shape of the first electrode 316 and the second electrode 318 can differ from one another.

The tip component 300 can have one or more ports 328A, 328B therein. This arrangement can facilitate removal of tissue, smoke and other material cut during operation of the tip component 300. For example, a first port 328A can be defined by the tip component 300 and can be in the first face 308 and a second port 328B can be defined by the tip component 300 and can be in the second face 312. The one or more ports 328A, 328B can be an inlet to a one or more lumens (shown subsequently such as in FIGS. 4 and 4A) that defines a flow channel. The one or more ports 328A, 328B can be in fluid communication with the flow channel defined by the one or more lumens. The one or more ports 328A, 328B via the one or more lumens can extend along the shaft 125 and can be in fluid communication with the flow channel 224 in handpiece 104 and further in communication with the aspiration tubing 222 which communicates with the negative pressure source 220 (FIG. 1). The location of the first port 328A and the second port 328B in FIG. 3B is purely exemplary and can be in other locations such as proximal of the tip component 300 or on another part of tip component 300 (not in the first or second face 308, 312). The use of a single port or additional ports are also contemplated.

Figure 4:
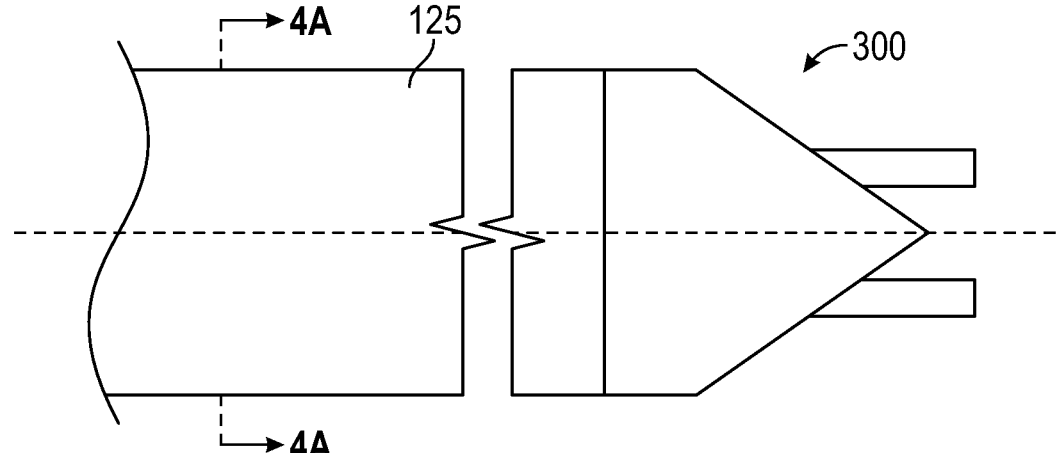
FIG. 4 is partially broken away view of an outer shaft and the distal (working) end of the probe of FIG. 2 according to an example of the present disclosure.
Figure 4A:
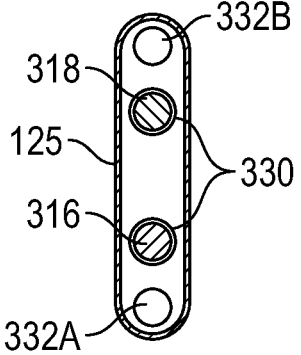
FIG. 4A is a cross-sectional view of the outer shaft of the probe of FIG. 4 according to an example of the present disclosure.

FIG. 4 shows the tip component 300 and the shaft 125. FIG. 4A is a cross-section through the shaft 125 showing the first and second electrode 316, 318, insulating material 330 around the first and second electrode 316, 318 and lumens 332A and 332B. As discussed the lumens 332A and 332B extend through the shaft 125 longitudinally from the handle to the tip component 300 and communicate with the first port 328A and the second port 328B, respectively. The lumens 332A and 332B are configured to transport tissue, smoke and other products of operations of the tip component 300 from the surgical site through the shaft 125. The lumens 332A and 332B can be in fluid communication with the flow channel 224 in handpiece 104 and further in communication with the aspiration tubing 222 which communicates with the negative pressure source 220 (FIG. 1).

Figure 5A:
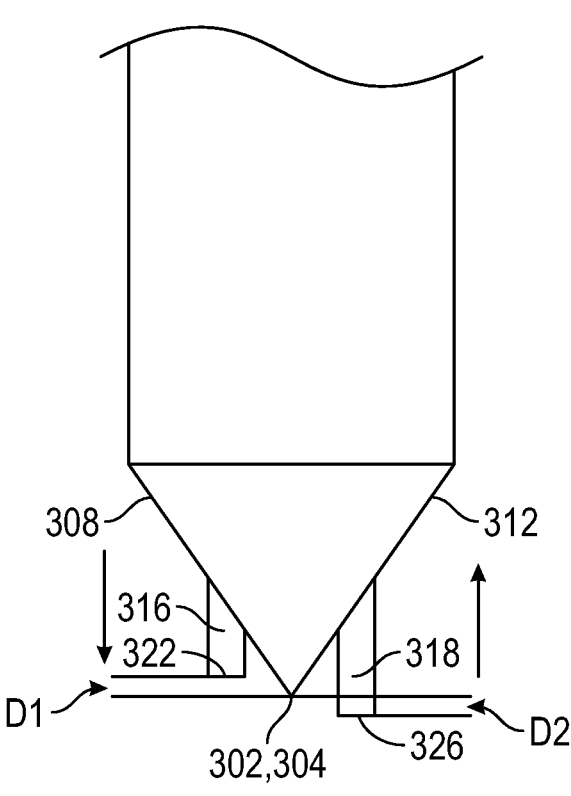
FIG. 5A is an enlarged plan view of the distal (working) end of the probe of FIGS. 2-4A according to another example with a first electrode and a second electrode undergoing reciprocal movement such that the first electrode is retracted a distance proximally relative to a sharp and the second electrode is extended a distance distally relative to the sharp according to an example of the present disclosure.
Figure 5B:
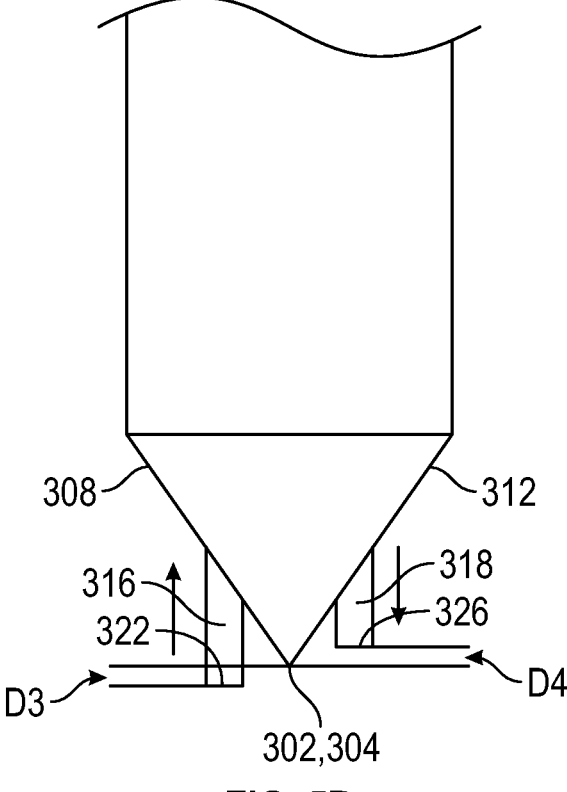
FIG. 5B is an enlarged plan view of the distal (working) end of the probe of FIGS. 2-4A with the first electrode and the second electrode undergoing the reciprocal movement such that the first electrode is extended a distance distally relative to the sharp and the second electrode is retracted a distance proximally relative to the sharp according to an example of the present disclosure.

FIGS. 5A and 5B show operation of the first and second electrodes 316, 318 according to one RF ablation mode. FIGS. 5A and 5B show that the first and second electrodes 316, 318 can both reciprocate relative to one another and to the other features of the tip component 300 including the sharp 302 at the distal end 304. The reciprocating movement of the first electrode 316 can be inverted relative to that of the second electrode 318. Thus, the movement of the first electrode 316 can be 180 degrees out of phase with the movement of the second electrode 318. As such, when the first electrode 316 is retracting (moved back proximally toward the first face 308) the second electrode 318 can be extending (moved outward distally from the second face 312). When the first electrode 316 reaches a fully retracted position as shown in FIG. 5A, the second electrode 318, at substantially the same time, reaches a fully extended position. It is contemplated that movement of the first electrode 316 relative to the second electrode 318 need not be inverted fully out of phase but could be offset in another manner.

As shown in FIG. 5A, the distal end 322 of the first electrode 316 can be distal of the point (the distal end 304) of the sharp 302 a distance D1. This distance D1 can be between 0.001 and 0.25 inches (0.0254 mm and 6.35 mm), for example. Preferably, D1 can be about 1 mm but can change based upon factors such as the distance the first electrode 316 is from the sharp 302. The distal end 326 of the second electrode 318 can be proximal of the point (the distal end 304) of the sharp 302 a distance D2. The distance D2 can be between 0.001 and 0.25 inches (0.0254 mm and 6.35 mm), for example. Preferably, D2 can be about 1 mm although this can vary depending on factors as discussed above.

FIG. 5B shows the first electrode 316 reaches a fully extended position and the second electrode 318, at substantially the same time, reaches a fully retracted position. In FIG. 5B, the distal end 322 of the first electrode 316 can be distal (the distal end 304) of the sharp 302 a distance D3. This distance D3 can be between 0.001 and 0.25 inches (0.0254 mm and 6.35 mm), for example. Preferably, D3 can be about 1 mm. The distal end 326 of the second electrode 318 can be proximal (the distal end 304) of the sharp 302 a distance D4. The distance D4 can be between 0.001 and 0.25 inches (0.0254 mm and 6.35 mm), for example. Preferably, D4 can be about 1 mm. Distances D1, D2, D3 and D4 need not be the same in all instances and can vary relative to one another.

The reciprocation rate of the first and second electrodes 316, 318 can be varied as desired by the surgeon (using one or more buttons 166a, 166b, 166c, etc. on the handpiece 104 of FIG. 1) or can be controlled according to algorithm as dictated by the controller 165 (FIG. 1) or other electronic device. It is contemplated the reciprocation of the first and second electrodes 316, 318 can be between 1,000 RPM and 30,000 RPM. It may be desirable in some operation modes to operate at a lower range of speed (e.g., 1,000 RPM to 3,000 RPM). Similarly other operation modes it may be desirable to operate at a higher range of speed (e.g., 5,000 RPM to 30,000 RPM).

The first and second electrodes 316, 318 can be configured as a bipolar electrode pair according to one example. However, the first and second electrodes 316, 318 can be monopolar according to other examples. With a bipolar electrode pair arrangement, the first electrode 316 can serve as a first polarity electrode and the second electrode 318 can serve as a second polarity electrode of the bipolar electrode pair. At least one of the first electrode 316 and the second electrode 318 can be in selective contact with tissue at any point during the treating of the tissue.

Figures 6A, 6B:
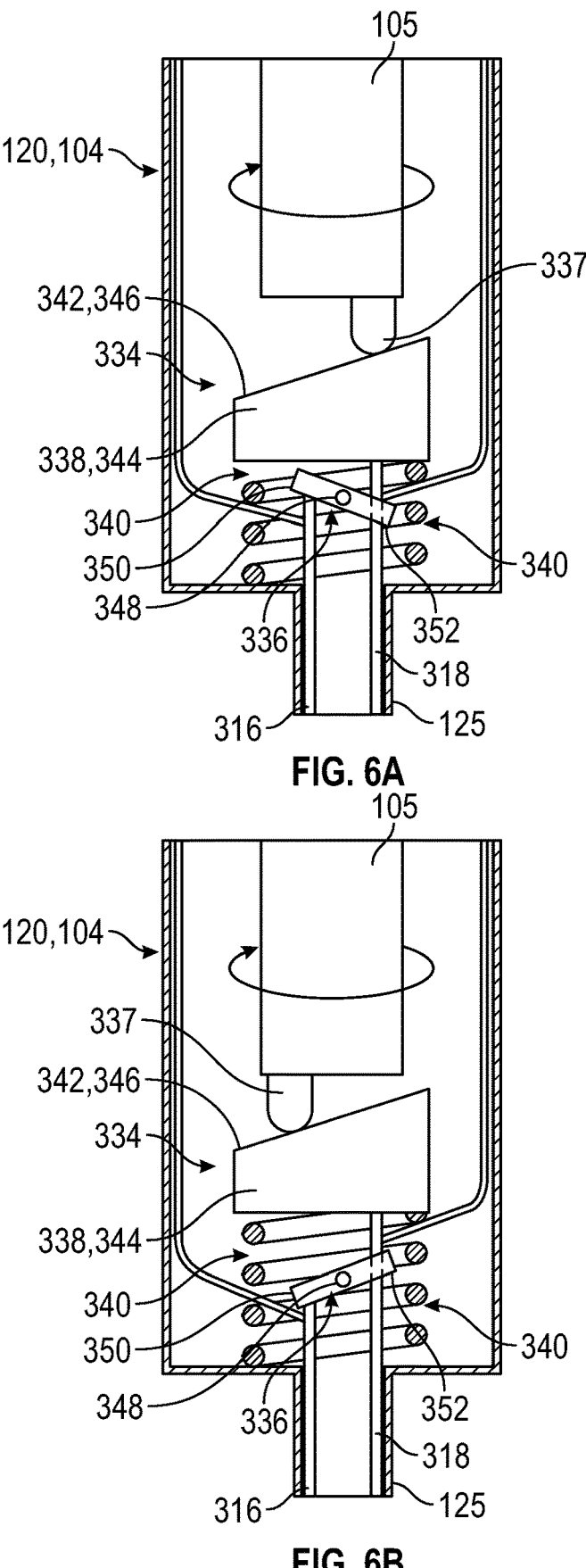
FIGS. 6A and 6B are a cross-sectional views of a hub and a portion of the outer shaft of the probe of FIGS. 1 and 2 showing operation of a cam mechanism and pivot arm to reciprocate the first electrode and the second electrode according to an example of the present disclosure.
Figures 7, 7A:
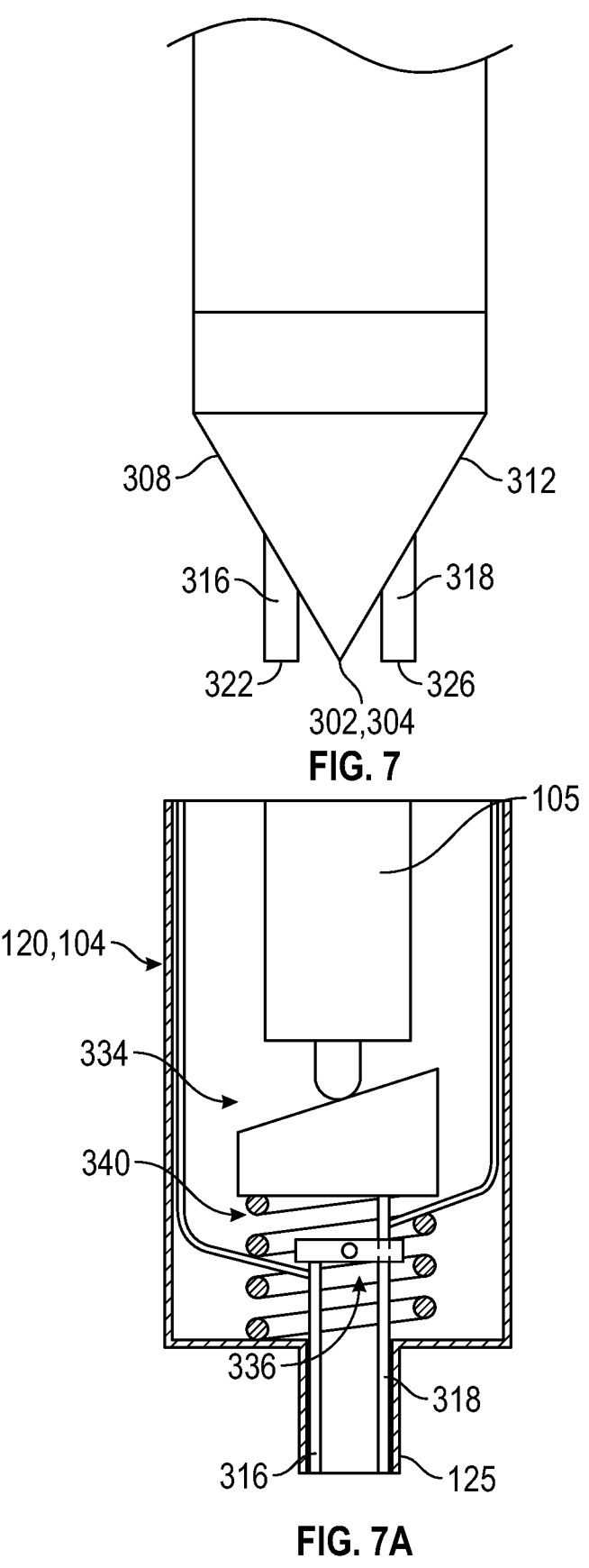
FIG. 7 is an enlarged perspective view of the distal (working) end of a probe of FIGS. 1 and 2 operating in a coagulation mode with the first electrode and the second electrode held in a stationary position adjacent the sharp according to an example of the present disclosure.
FIG. 7A is a cross-sectional view of the hub of the probe of FIGS. 1 and 2 with the cam mechanism and pivot arm held in a neutral position for the coagulation mode to position the first electrode and second electrode as shown in FIG. 7 according to an example of the present disclosure.

FIGS. 6A and 6B show how the first and second electrodes 316, 318 can be reciprocated from the hub 120 and/or handpiece 104. FIGS. 6A and 6B are cross-sectional views of the hub 120 and a portion of the shaft 125. FIGS. 6A and 6B show the motor drive 105 (or a mechanism such as a shaft coupled to the motor drive 105). The motor drive 105 can extend into the hub 120. The first and second electrodes 316, 318 are shown in FIGS. 6A and 6B with the recognition another component such as shafts, wires, rods, etc. could be substituted for the first and second electrodes 316, 318. The shafts, wires, rods etc. could be directly or indirectly coupled to the first and second electrodes 316, 318 adjacent the distal tip. Thus, the first and second electrodes 316, 318 need not extend into the hub 120 as illustrated.

FIGS. 6A and 6B show operation a cam mechanism 334 and a linkage arm 336 (sometimes called a pivot arm herein) to reciprocate the first electrode 316 and the second electrode 318. The cam mechanism 334 can include a driver 337, a following component 338 and a spring 340. The following component 338 can have a camming surface 342 and a body 344. The camming surface 342 can have one or more undulations or peaks 346, for example.

As shown in FIGS. 6A and 6B, the driver 337 can be coupled to or can be part of the drive motor 105. The following component 338 can be coupled with the spring 340. The spring 340 can force the following component 338 against the driver 337. More particularly, the driver 337 can engage the camming surface 342 of the following component 338 via force of the spring 340. The spring 340 can engage a distal end of the body 344. The camming surface 342 can be shaped as desired such as by having one or more undulations or peaks 346. Although a single undulation (peak) is shown in FIGS. 6A and 6B, multiple undulations (waves or peaks) are contemplated according to some examples.

The shape of the camming surface 342 can cause the body 344, and indeed the entire following component 338 to move proximal-distal within the hub 120 (i.e., the shape of the camming surface 342 causes relative extension and compression of the spring 340). As one of the first electrode 316 or the second electrode 318 is coupled to the body 344, movement of the body 344 translates the one of the first electrode 316 or the second electrode 318 within the shaft 125 as shown in FIGS. 6A and 6B.

The linkage arm 336 can be positioned adjacent the cam mechanism 334 such as within the hub 120. The linkage arm 336 can include a pivot 348, a first arm 350 and a second arm 352. The first electrode 316 can couple with the linkage arm 336 at the first arm 350. The second electrode 318 can couple with the linkage arm 336 at the second arm 352 and can pass through the second arm 352 to couple with the body 344. The pivot 348 can be positioned between the first arm 350 and the second arm 352. The first electrode 316 does not couple with and is spaced from the body 344. It should be noted that the example of FIGS. 6A and 6B is purely exemplary and the first electrode 316 could couple with the body 344 in other examples rather than the second electrode 318.

FIG. 6A shows an arrangement with the linkage arm 336 tilted to a first position. This first position of the linkage arm 336 translates the first electrode 316 to be retracted proximally to the fully retracted position shown previously in FIG. 5A. In contrast, the orientation of the linkage arm 336 in the first position translates the second electrode 318 to be extended distally to the fully distally extended position shown previously in FIG. 5A.

FIG. 6B shows another arrangement with the linkage arm 336 tilted to a second position. This second position of the linkage arm 336 translates the first electrode 316 to be extended distally to the fully distally extend position shown previously in FIG. 5B. In contrast, the orientation of the linkage arm 336 in the second position translates the second electrode 318 to be retracted proximally to the fully retracted position shown previously in FIG. 5B.

Movement of the linkage arm 336 is tied to the cam mechanism 334 as the second electrode 318 is coupled to the body 344. As the position of the body 344 shifts proximal-distal (as dictated by interaction of the driver 337 with the camming surface 342), the linkage arm 336 will pivot on the pivot 348 between the first position and the second position and back to the first position and so forth in a reciprocating manner.

Various mechanisms can be used to perform actuation of the second electrode 318 and the first electrode 316 to perform the reciprocation are described herein. One example is provided above, however, additional or alternative mechanisms are described in the various applications incorporated by reference with the U.S. Application Publications noted above. Such mechanisms can be coupled to the drive mechanism 105 to be driven thereby and can include any one or combination of gears, shafts, cams, linear drives, ratchets, collars, springs, etc.

FIG. 7 shows the distal end 112 of the shaft 125 of the probe 110 with the first electrode 316 and the second electrode 318 arranged and operating in a coagulation mode. According to this arrangement and mode of operation the electrical power can be lowered relative to the ablation mode and the first electrode 316 at the distal end 322 can be substantially flush (within ±0.1 mm) with the point (the distal end 304) of the sharp 302. Similarly, the second electrode 318 at the distal end 326 can be substantially flush (within ±0.1 mm) with the point (the distal end 304) of the sharp 302. Thus, the first electrode 316 and the second electrode 318 can be arranged to extend substantially a similar distance at the distal end 112 as measured from the first face 308 and the second face 312, respectively. The point (the distal end 304) of the sharp 302 can be formed of an electrically non-conductive material, and therefore, can act as a dielectric barrier that prevents arcing between the first and second electrodes 316, 318.

FIG. 7A illustrates how the first and second electrodes 316, 318 can be positioned in the manner of FIG. 7. FIG. 7A shows the hub 120, where the motor drive 105 rotation has been halted in a desired (neutral) position. This position allows for a neutral position for the cam mechanism 334 which pivots the linkage arm 336 to a neutral position via the coupling of the second electrode 318 with both the linkage arm 336 and the cam mechanism 334 (via the body 344). The neutral position of the linkage arm 336 can position the linkage arm 336 between the first position and the second position previously illustrated in FIGS. 6A and 6B, respectively. The neutral position for the linkage arm 336 can be one that orients the linkage arm 336 substantially perpendicular to a longitudinal axis of the shaft 125, for example. The linkage arm 336 can be maintained in the neutral position by the spring 340. Optionally locking features (e.g., tabs, hooks, etc.) could be utilized to secure the linkage arm 336 in the neutral position.

Figure 8A:
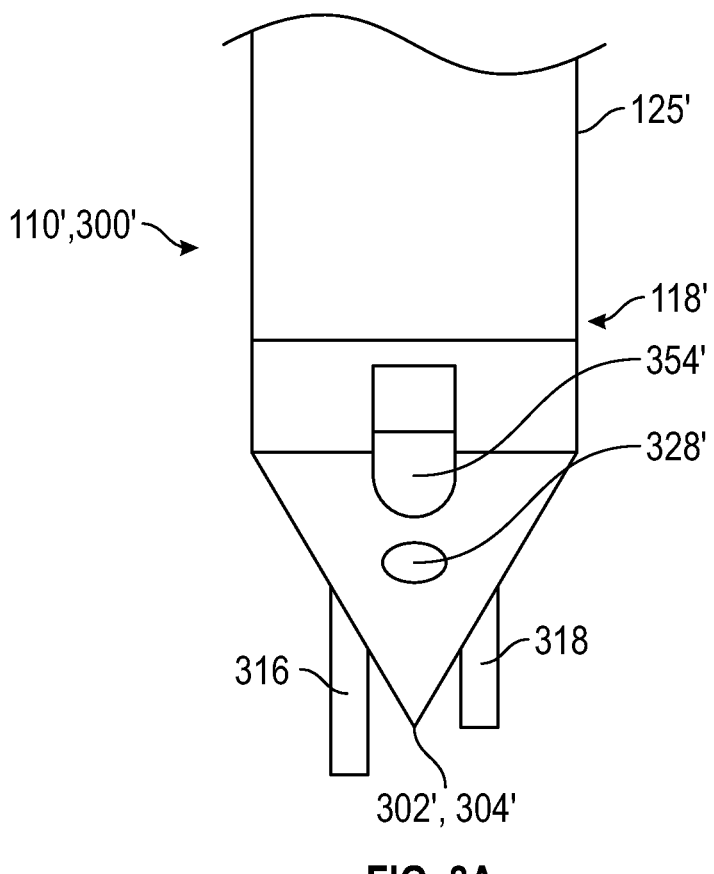
FIG. 8A is an enlarged first plan view of the distal (working) end of a probe that has a pointed tip according to another example of the present disclosure.
Figure 8B:
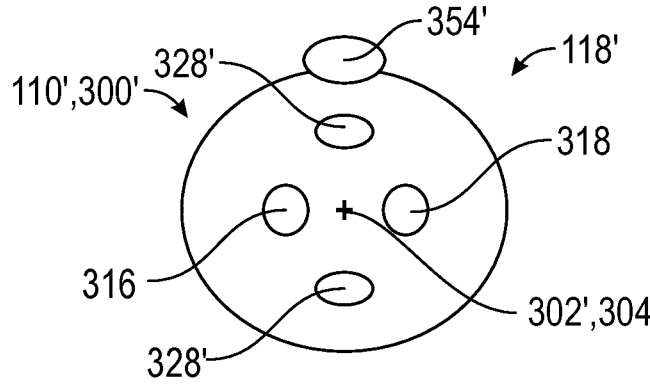
FIG. 8B is an enlarged second plan view of a distal (working) end of the probe of FIG. 8A showing various components thereof according to an example of the present disclosure.

FIGS. 8A and 8B illustrate a distal end 112' of a shaft 125' of a probe 110' with a tip component 300' similar to that of the probe 110 of FIGS. 1-7A. In the interest of brevity, construction of the probe 110' and tip component 300' will not be discussed other than to focus on differences between the tip component 300 and the tip component 300'. The tip component 300' can include a sharp 302' at a distal end 304'. However, rather then being an elongate cutting edge as was the case with the example of FIG. 1-7A, the sharp 302' can be a point such as used for puncturing tissue. The first and second electrodes 316, 318 can be constructed in the manner previously discussed and can reciprocate (or be held in the coagulation position) as previously discussed. The tip component 300' can have one or more ports 328' therein for evacuation of tissue debris in the manner previously discussed.

The tip component 300' can include an illumination element 354'. The illumination element 354' can be positioned at or adjacent the tip component 300' such as adjacent but proximal of the distal end 304'. The illumination element 354' can be a light emitting diode (LED) or plurality of LEDs for example. The illumination element 354' can be actuated and controlled by the buttons on the handpiece, foot pedal, etc. The illumination element 354' can increase or decrease in luminance, change illumination color, etc. under control such as actuated by the buttons on the handpiece as contemplated herein. Although a single illumination element 354' is shown, it is contemplated a plurality of such illumination elements can be utilized at or adjacent the distal end 304'. Other locations for the illumination element 354' are also contemplated.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The term "substantially", "generally" or "about" mean within 15% of the value provided. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A probe for an electrosurgical device for treating tissue, the probe comprising:

a tip having a sharp at a distal most end thereof, a first electrode adjacent the sharp on a first side thereof, and a second electrode adjacent the sharp on a second side thereof, wherein the first electrode is spaced from the second electrode;

wherein the sharp comprises an edge and the tip includes a first distal face extending laterally and longitudinally from the edge and a second distal face extending laterally and longitudinally from the edge, wherein the first distal face includes a first aperture receiving the first electrode and the second distal face includes a second aperture receiving the second electrode;

wherein the first electrode and the second electrode are configured to reciprocate relative to the tip to selectively move between a first configuration where a distal end of first electrode is distal of the sharp and a distal end of the second electrode is proximal of the sharp and a second configuration where the distal end of the first electrode is proximal of the sharp and the distal end of the second electrode is distal of the sharp.

2. The probe of claim 1, wherein at least one of the first distal face or the second distal face includes at least a port configured for vacuum aspiration of fluid including tissue debris from adjacent the tip.

3. The probe of claim 2, further comprising an elongate outer shaft having a proximal end, a distal end and defining one or more passages extending therein from the proximal end to the distal end, wherein the tip is coupled to or forms the distal end of the outer shaft.

4. The probe of claim 3, wherein at least one of the one or more passages is in fluid communication with the port.

5. The probe of claim 1, wherein the first electrode is spaced from the second electrode by between 0.02 inches and 0.08 inches, inclusive.

6. The probe of claim 1, wherein the tip is an electrically non-conductive material.

7. The probe of claim 6, wherein the tip is a ceramic or ceramic composite and wherein the sharp is one of an edge or point.

8. The probe of claim 1, wherein the first electrode and the second electrode are tungsten or an alloy containing tungsten.

9. The probe of claim 1, wherein the first electrode and the second electrode have a diameter of between 0.01 inches and 0.02 inches, inclusive.

10. The probe of claim 1, wherein the distal end of the first electrode and the second electrode is moved distal of the sharp by between 0.001 inches and 0.25 inches, inclusive.

11. The probe of claim 1, further comprising an illumination device adjacent the tip.

12. The probe of claim 1, further comprising a cam mechanism and a linkage arm, wherein the cam mechanism is coupled to one of the first electrode and the second electrode and the linkage arm is coupled to both the first electrode and the second electrode.

13. The probe of claim 1, further comprising a handle, wherein the probe is configured to couple with the handle.

14. The probe of claim 1, wherein the probe is configured with an electrosurgical coagulation mode that halts reciprocation of the first electrode and the second electrode and positions the first electrode and the second electrode in a substantially stationary arrangement adjacent the sharp.

15. The probe of claim 14, wherein in the electrosurgical coagulation mode a distal end of the first electrode and a distal end of the second electrode are substantially flush with a tip of the sharp.

16. The probe of claim 1, the first electrode serves as a first polarity electrode and the second electrode serves as a second polarity electrode of a bipolar electrode pair, wherein the probe is configured for electrosurgical resection and electrosurgical coagulation of the tissue.

17. The probe of claim 16, wherein at least one of the first electrode and the second electrode is in selective contact with the tissue at any point during the treating of the tissue.

18. A probe for an electrosurgical device for treating tissue, the probe comprising:

a tip having a sharp at a distal most end thereof;

a first electrode adjacent the sharp on a first side thereof;

a second electrode adjacent the sharp on a second side thereof, wherein the first electrode is spaced from the second electrode; and a cam mechanism and a linkage arm, wherein the cam mechanism is coupled to one of the first electrode and the second electrode and the linkage arm is coupled to both the first electrode and the second electrode;

wherein the first electrode and the second electrode are configured to reciprocate relative to the tip to selectively move between a first configuration where a distal end of first electrode is distal of the sharp and a distal end of the second electrode is proximal of the sharp and a second configuration where the distal end of the first electrode is proximal of the sharp and the distal end of the second electrode is distal of the sharp; and wherein the cam mechanism includes a surface with undulations.

19. A probe for an electrosurgical device for treating tissue, the probe comprising:

a tip having a sharp at a distal most end thereof;

a first electrode adjacent the sharp on a first side thereof; and a second electrode adjacent the sharp on a second side thereof, wherein the first electrode is spaced from the second electrode;

wherein the first electrode and the second electrode are configured to reciprocate relative to the tip to selectively move between a first configuration where a distal end of first electrode is distal of the sharp and a distal end of the second electrode is proximal of the sharp and a second configuration where the distal end of the first electrode is proximal of the sharp and the distal end of the second electrode is distal of the sharp; and wherein the reciprocation of the first electrode and the second electrode is between 1,000 RPM to 30,000 RPM, inclusive.

* * * * *